(12) United States Patent
Loeb et al.

(10) Patent No.: US 7,970,477 B2
(45) Date of Patent: Jun. 28, 2011

(54) METHOD AND APPARATUS FOR DETECTING OBJECT ORIENTATION AND POSITION

(75) Inventors: Gerald E. Loeb, South Pasadena, CA (US); Wei Tan, Overland Park, KS (US)

(73) Assignee: Mann Medical Research Organization, Santa Clarita, CA (US)

( * ) Notice: Subject to any disclaimer, the term of this patent is extended or adjusted under 35 U.S.C. 154(b) by 0 days.

(21) Appl. No.: 11/679,109

(22) Filed: Feb. 26, 2007

(65) Prior Publication Data
US 2007/0270722 A1 Nov. 22, 2007

Related U.S. Application Data

(63) Continuation of application No. 11/457,101, filed on Jul. 12, 2006, now abandoned.

(60) Provisional application No. 60/698,313, filed on Jul. 12, 2005.

(51) Int. Cl.
*A61N 1/05* (2006.01)
(52) U.S. Cl. ......................................................... 607/48
(58) Field of Classification Search .................... 607/48, 607/49, 62; 600/587, 595
See application file for complete search history.

(56) References Cited

U.S. PATENT DOCUMENTS

| | | | |
|---|---|---|---|
| 4,424,812 A | 1/1984 | Lesnick | |
| 4,945,305 A | 7/1990 | Blood | |
| 5,193,539 A | 3/1993 | Schulman | |
| 5,193,540 A | 3/1993 | Schulman | |
| 5,255,345 A | 10/1993 | Shaefer | |
| 5,312,439 A | 5/1994 | Loeb | |
| 5,324,316 A | 6/1994 | Schulman | |
| 5,953,683 A | 9/1999 | Hansen et al. | |
| 6,164,284 A * | 12/2000 | Schulman et al. | 128/899 |
| 6,175,764 B1 | 1/2001 | Loeb | |
| 6,176,837 B1 * | 1/2001 | Foxlin | 600/595 |
| 6,400,139 B1 | 6/2002 | Khalfin | |
| 6,447,448 B1 | 9/2002 | Ishikawa et al. | |
| 6,528,991 B2 | 3/2003 | Ashe | |
| 6,624,626 B2 | 9/2003 | Khalfin | |
| 6,658,301 B2 | 12/2003 | Loeb et al. | |
| 6,690,963 B2 | 2/2004 | Ben-Haim | |
| 7,295,877 B2 * | 11/2007 | Govari | 607/60 |
| 2005/0004450 A1 * | 1/2005 | Ben-Haim et al. | 600/424 |
| 2005/0137648 A1 * | 6/2005 | Cosendai et al. | 607/48 |
| 2005/0171577 A1 * | 8/2005 | Cohen et al. | 607/48 |
| 2005/0245821 A1 * | 11/2005 | Govari et al. | 600/429 |
| 2006/0016452 A1 * | 1/2006 | Goetz et al. | 128/899 |
| 2006/0058646 A1 * | 3/2006 | Viswanathan | 600/434 |

* cited by examiner

*Primary Examiner* — Scott M Getzow
*Assistant Examiner* — Amanda Patton
(74) *Attorney, Agent, or Firm* — Malcolm J. Romano; Oleh J. Sajac (57) ABSTRACT

A signal transmitting and receiving system to track the position and orientation of limb segments in order to provide feedback information for the control of the limb movement. The user will generally be seated in a wheelchair that provides a structure upon which orthogonal and/or non-orthogonally oriented coils can be mounted and energized selectively so as to create variously oriented magnetic fields. Multiple wireless sensors injected into the limb detect the local field strength and send information telemetrically to a central controller. The controller extracts information about the position and orientation of each limb segment by combining signals from various sensors according to calibration information and optimal filtering methods for extracting information from multiple nonlinear sensors in mechanically constrained systems.

18 Claims, 7 Drawing Sheets

METHOD AND APPARATUS FOR DETECTING OBJECT ORIENTATION AND POSITION

CROSS REFERENCE TO RELATED APPLICATIONS

This United States patent application is a continuation of U.S. application Ser. No. 11/457,101, filed Jul. 12, 2006, now abandoned entitled "Method and Apparatus for Detecting Object Orientation and Position," which is related to and claims the benefit of the filing date of U.S. Provisional Patent Application Ser. No. 60/698,313, filed Jul. 12, 2005, entitled "Method and Apparatus for Detecting Object Orientation and Position," the contents of both of which are incorporated herein by reference. This United States patent application is also related to co-pending U.S. patent application Ser. No. 11/457,004, also filed on Jul. 12, 2006, entitled "Probe for Identifying Injection Site for Deep Brain Neural Prostheses," inventor Gerald E. Loeb, the contents of which are also incorporated herein by reference.

BACKGROUND OF THE INVENTION

1. Field of the Invention

The present invention relates generally to implanted devices and methods for detecting object orientation and position.

2. General Background and State of the Art

Wireless micro-stimulators such as the BION® implants (U.S. Pat. Nos. 5,193,539, 5,193,540, 5,312,439, and 5,324,316; herein incorporated by reference) can be injected into paralyzed muscles or the stumps of amputated limbs to restore voluntary control of limb movement. In order to control neuromuscular stimulation, it is desirable to provide information about the posture and movement of the limb. Two sources of such information can be distinguished. The first derives from the fact that most patients will have residual voluntary control over some portions of the limb. Such voluntary movements can be sensed by the present invention in order to provide command information about the patient's intended limb movements. The second derives from the use of feedback information to improve motor performance. The movements produced by stimulation of the muscles can be sensed by the present invention, thereby providing feedback signals that modify the electrical stimulation pattern in order to achieve the desired limb movement. In both cases, it is desirable to employ sensors that are no more intrusive than the injectable stimulators themselves. Furthermore it is desirable to minimize the number of separate devices that must be injected into the patient while maximizing the information that is available for control of the prosthetic system.

There are many technologies for tracking and measuring limb movement in the laboratory but these generally require physically affixing sensors or markers to the surface of the limb. Most commonly, the position and/or orientation of these sensors or markers are determined by capturing optical information by video cameras or photodiode arrays whose position and line of sight must be carefully determined and maintained. Search coil systems use large coils to create homogeneous, orthogonally oriented magnetic fields around the subject, which are detected by a detection coil such as attached to a contact lens to track eye movement. Polhemus Technology (U.S. Pat. Nos. 6,624,626 and 6,400,139) and Ascension Technology (U.S. Pat. Nos. 6,528,991, 5,953,683, and 4,945,305) use externally mounted sensors consisting of three orthogonal detection coils to detect the relative strength of a magnetic field created by an external field generator. In these magnetic sensing systems, the magnetic sources can be AC (U.S. Pat. No. 6,690,963), DC (U.S. Pat. No. 4,945,305) or sourceless (U.S. Pat. No. 5,953,683 earth magnetic field). There are also mechanical transducers such as electrogoniometers produced by Infotronic Company that can be affixed across adjacent limb segments to detect angular rotation of the joint in one or two axes.

The prior art includes a fully implanted sensor of a single joint angle based on the effect of a permanent magnet on a nearby Hall-effect sensor. The magnet is implanted in the bone on one side of the joint and the Hall-effect sensor is implanted on the other side of the joint so that changes in joint angle produce a systematic change in the relative orientation of the sensor to the magnet. The sensor is connected by electrical leads to an implanted signal processor that, in turn, transmits data by wireless telemetry to an external controller.

The prior art includes a sensing system to track the tip of an intravascular catheter as it is maneuvered within a patient (U.S. Pat. No. 6,690,963). This system uses a large external array of magnetic coils to create a magnetic field that is sensed by orthogonal sensing coils contained within the tip of the catheter. In the preferred embodiments of the invention the coils have mutually orthogonal axes. The coils are closely spaced along the axis of the catheter. The magnetic field generating coils are arranged across the surface of the table on which the subject lies. The sensing coils are connected by electrical leads passing along the catheter to external signal processing instrumentation. This system basically uses the same mechanism as the concentrated orthogonal 3-axis magnetic sensor mentioned above. Sensing coils with distributed positions and orientations will present more than one local minimum points in the problem. Algorithms without global optimization technique tend to set design limitations on sensing coil arrangement such that the coils are close enough to the concentrated and orthogonal configuration.

Various algorithms have been described to transform the amplitude and phase information detected by sensors into conventional coordinate frames. Both rotation matrix and quaternion have been used to provide complete descriptions of 3-D orientations and rotation transforms. Mathematical methods exist to convert between them or combine them into hybrid representations. The data processing methods include both iterative and non-iterative techniques. U.S. Pat. No. 6,690,963 teaches numerical algorithm to solve the nonlinear equation group. But it does not investigate the local minimum points associated with the numerical process. In fact, if the receiving coils and transmitting coils are not arranged properly, there will be local minimum areas that the conventional numerical methods mentioned in this patent cannot solve. In the prior arts, the filters applied to the sensing system include mean-square filters and Kalman filters. The selection of appropriate methods for computing and describing position and orientation is an important part of the design of a sensing system that determines its practicality and performance in a given application.

SUMMARY

In one aspect of the position and orientation detecting devices, a method to detect human limb posture comprises injectable distributed sensors of externally generated RF electromagnetic fields. These sensors and transmitters can be arranged at different locations with respect to the limb and they are allowed to have non-orthogonal and/or nonconcentric orientations with respect to each other, instead of being lumped in a single package as a 3-axis assembly. Keeping these sensors distributed instead of in the same package and making them nonorthogonal offers more freedom especially in medical applications such as control of Functional Electrical Stimulation (FES). In FES control, a preferable design is to have sensors and nerve stimulators packaged in the same implantable micro-capsule. Wireless sensors that are implanted into the human body need to be physically small and to function with low power consumption. The distributed scheme makes possible a sensing system with single-axis search coil sensors each of which can be packaged into an elongated micro-capsule that can be injected into the limb rather than requiring open surgical implantation. In an exemplary embodiment, the sensing coil is the same as is already required in the implanted microcapsule in order to receive power from and exchange data with an external controller.

In another aspect of the position and orientation detecting devices, a remote human limb position and orientation determining system comprises a plurality of radiating antenna coils to generate RF magnetic fields and a group of single axis micro-miniature sensing capsules with size and form factor suitable for injection into human limbs. Data acquisition, signal transmitting and receiving circuits are also in the capsules. The data can be sent by electromagnetic telemetry to an external coil. The external coil relays the data to a microcomputer, which acts as a signal processing unit.

In yet another aspect of the position and orientation detecting devices, synchronizing techniques enable the system to get not only the amplitude, but also the phase of the RF magnetic signal. The combining of phase and amplitude information makes the best use of the sensor output and is suitable for medical applications, which requires as few implants as possible. Various schemes are possible for gating and modulating the electromagnetic fields generated by each of the external coils sequentially or simultaneously and relating the state of the transmitters to the amplitude and/or phase of the signals detected at known times by each sensor.

In still a further aspect of the position and orientation detecting devices, the computing algorithms comprise a composite optimization process including genetic algorithm and gradient based local optimization. The algorithm produces position and orientation information based on the sensor signals. The information is then fed through an Extended Kalman Filter to suppress noise. The solution is accurate, fast and continuous.

BRIEF DESCRIPTION OF THE DRAWINGS

Aspects of the present invention are illustrated by way of example, and not by way of limitation, in the accompanying drawings, wherein.

DETAILED DESCRIPTION

The detailed description set forth below is intended as a description of exemplary embodiments of the present invention and is not intended to represent the only embodiments in which the present invention can be practiced. The term "exemplary" used throughout this description means "serving as an example, instance, or illustration," and should not necessarily be construed as preferred or advantageous over other embodiments. The detailed description includes specific details for the purpose of providing a thorough understanding of the present invention. However, it will be apparent to those skilled in the art that the present invention may be practiced without these specific details. In some instances, well-known structures and devices are shown in block diagram form in order to avoid obscuring the concepts of the present invention.

Figure 1:
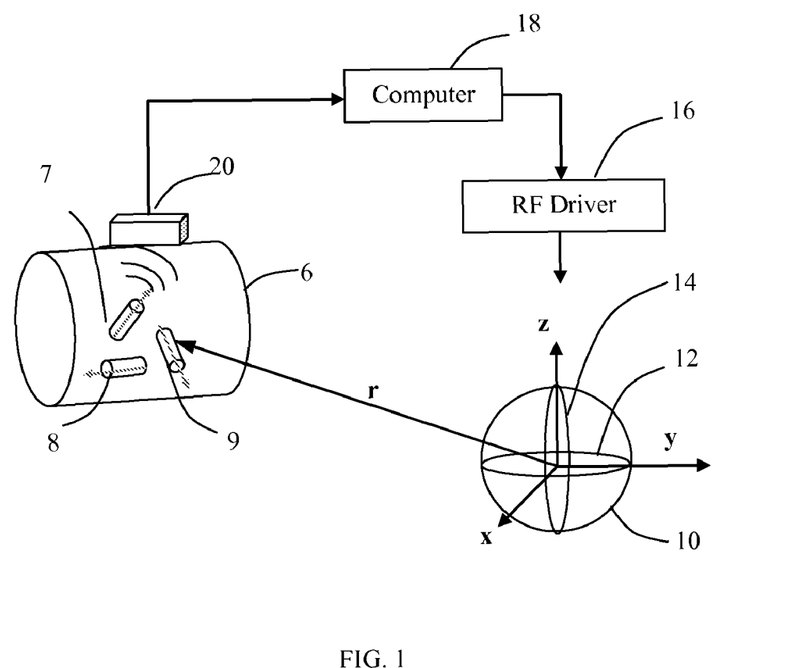
FIG. 1 is a schematic diagram of the position and orientation sensing system with distributed RF magnetic sensors and lumped transmitters.

In FIG. 1, a functional diagram of the distributed sensing system is illustrated. A multi-dimensional AC magnetic source 20 (that includes several inductive coils) energized by a RF driver 16 according to electronic signals from a controller 5 (not shown). Each inductive coil is excited for a small period of time, either sequentially or simultaneously with various patterns of modulation as described below. The inductive coils are energized by radio frequency sine waves, in this case, on the order of 500 kHz, so as to create magnetic fields that are received by one or more variously located and oriented sensors 7, 8 and 9 implanted within one or more body segments 10. Sensors 7, 8 and 9 transmit data regarding the signals that they detect to a receiver 6. The controller 5 computes the position and orientation of body segments 10 according to an algorithm that takes into consideration the data obtained from the sensors via the receiver 6 and the state of energization of the inductive coils at the time the sensor measurements were obtained.

Figure 2:
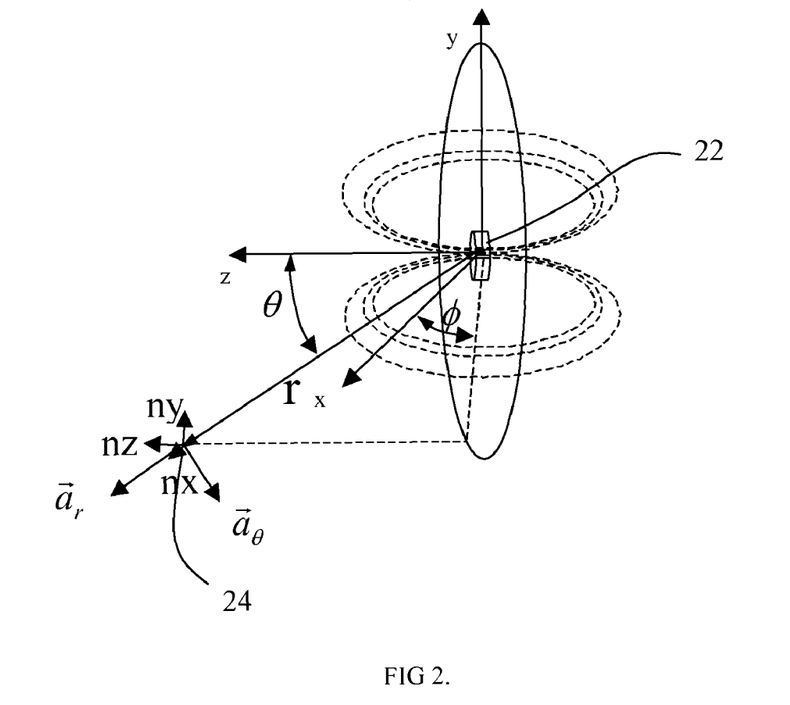
FIG. 2 illustrates the RF magnetic field at a certain point generated by a dipole antenna.

The inductive coils are likely to be non-concentric and similar or smaller in size to the distances between each other and between the coils and the sensors. This is substantially different from electromagnetic position sensing technologies employed in the prior art, in which very large coils are used to create uniform fields in the vicinity of sensors or in which very small coils are used to create uniform gradients in field strength in the vicinity of the sensors. As illustrated in FIG. 2, the magnetic field around each planar coil is toroidal. The strength of the signal measured by a given sensor from the magnetic field created by a given inductive coil depends complexly on their relative location and orientation, here described by a 3-axis Cartesian coordinate system and a 3-axis rotational coordinate system, respectively. The summation of magnetic fields created by simultaneous energization of two or more inductive coils depends on their relative positions and orientations and the amplitude, frequency and phase of their energization.

One Exemplary Embodiment of the Present Magnetic Sensor

Functional electrical stimulation (FES) of paralyzed muscles has traditionally focused on getting muscles to produce the requisite torques required for limb movement.

Micro-implants called BION® implantable microstimulators (BION is a registered trademark of Boston Scientific Neuromodulation Corporation, Reg. No. 2455608) have been developed to interface with the multiple muscles required for most tasks. They are modularly designed wireless capsules that can be injected into the human body without requiring surgery. Separately addressable BION's (selectively used as a noun hereinafter merely for convenience purposes) can be implanted at various sites in the body near motor nerves, where they receive power and digital command data from an external RF coil and deliver stimulating current pulses to recruit the motor neurons and activate associated muscles. Given appropriate control strategies, this technology could be used to create functional movement in limbs paralyzed by upper motor neuron disorders such as spinal cord injury and stroke.

As the functions to be implemented by BIONs become more demanding, the prosthetic system may include a growing armamentarium of sensors to detect voluntary command signals and to provide sensory feedback to regulate neuromuscular stimulation. Furthermore, these sensors and actuators may be readily combinable into custom configurations to deal with the inherent heterogeneity of patients with diverse physiognomies and lifestyles suffering from wide ranges of traumatic and neurological deficits. Attaching and wiring miscellaneous sensors on the body is not an attractive design for most scenarios of FES application, however. Activities of daily living such as bathing and sleeping require frequently detaching and re-attaching these sensors, which may be difficult and which is likely to result in problems with system calibration. External sensors are likely to be uncomfortable and vulnerable to damage. In an exemplary embodiment, the sensors may be integrated with the implants for one-time injection and long-term usage. The micro-coil within each BION implant may act as a magnetic sensor.

Figure 4:
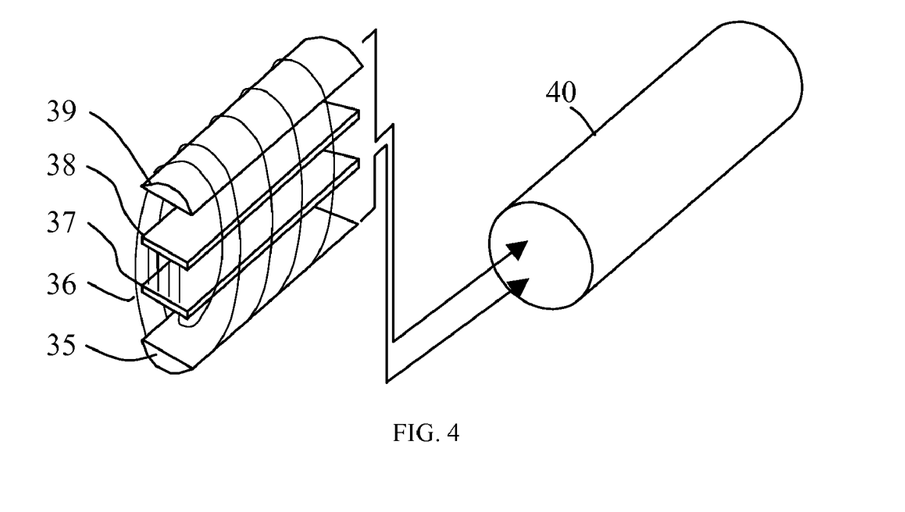
FIG. 4 illustrates the preferred implementation of a micro-miniature sensor assembly.

FIG. 4 illustrates an exemplary sensing coil structure. Several technologies may be used for building a magnetic sensor, including but not limited to those associated with search-coil magnetometer, flux gate magnetometer, or Hall effect sensors. A search-coil structure (a coil with ferrite material inserted inside) may provide good sensitivity and at the same time offers possibilities for wireless and micro-assembly implementation. Sensors of this type can detect magnetic fields as weak as $10^{-6}$ Gauss.

Also, as illustrated in FIG. 4, the sensor comprises two ferrite rods 35 and 39, an integrated circuit chip 38 with signal processing and communication circuits, a micro-PCB board 37 acting as a mechanical support and as an electrical connection base for the ASIC, a copper wire 36 around the laminated assembly, and a biocompatible capsule used as a case for the assembly. In FES control application, the stimulating parts can be packaged in the same capsule 40 with the sensor coil. In this case the coil can be re-used as the antenna for the stimulator. An alternative design consists of winding the coil on a thin-walled ferrite tube (As described in the Loeb and Tan Appendix). Other geometries are familiar to those with skill in the art. Some embodiments may comprise an elongated coil wrapped around a magnetic core material plus sensing and signal processing electronics so as to detect and measure a RF magnetic field.

Figure 5:
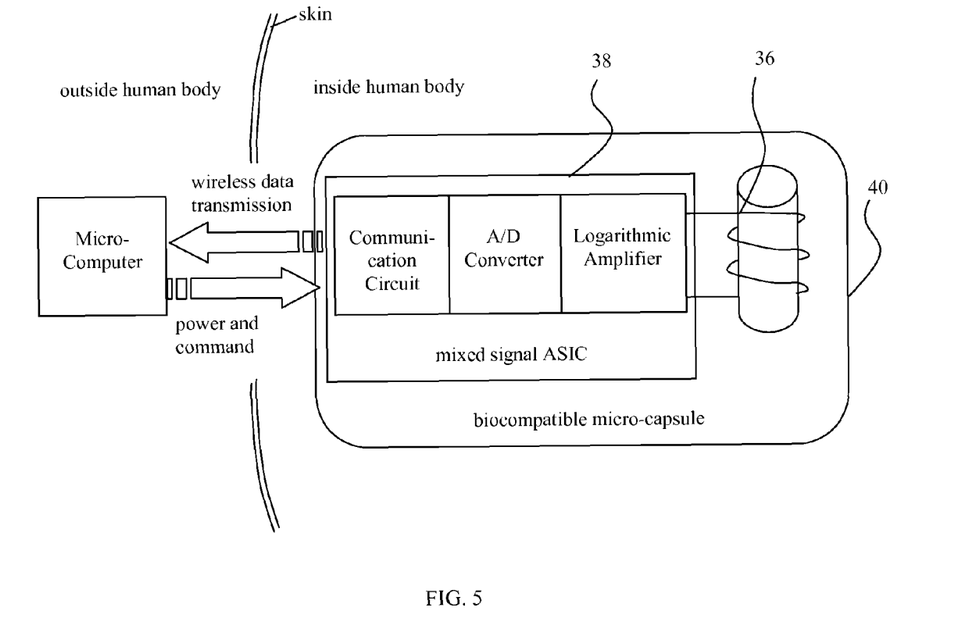
FIG. 5 illustrates the architecture of the sensor system working inside and outside of human body.

FIG. 5 illustrates the architecture of an exemplary sensor system including the single-axis magnetic sensor. A sensor coil senses the strength of the RF magnetic field as the induced voltage. Since the induced voltage drops with the third power of the distance between the sensor and the transmitter, the voltage signal is then amplified by a logarithmic amplifier. The logarithmic amplifier is used to compensate the cubic relationship and guarantee high dynamic range of the signal. The amplified signal is digitized and data regarding its amplitude and/or phase are transmitted to a controller using telemetry.

RF Magnetic Signal from a Dipole Ring Antenna

The BION implant consists of an electronic subassembly with an integrated circuit chip surrounded by a hermetically sealed glass capsule with external electrodes. The BION also includes a cylindrical coil around a hollow ferrite core that is the antenna of the implant. The coil is connected to the input pads of an ASIC through a ceramic hybrid substrate. In normal operation, it receives power and command data from a frequency-modulated RF magnetic field generated from an external coil worn in the vicinity of the implants. The strength of the received signal depends on the relative distance and orientation between the external and internal coil. The normal external coil can be turned off briefly while one or more other external coils in known positions are used to create a magnetic field for the implant coil to detect. The measured field strength will be sent by reverse telemetry to an external controller that will compute the position and orientation of the implant with respect to one or more such external reference coils. The antenna coil of the Bion implant is used as a magnetic sensor.

In the following description the coordinates for a coil is established according to these rules:
a. Z axes is defined as the direction according to right-hand rule applied to the positive direction of the coil current.
b. X and Y axes are orthogonal to Z and the sequence of X-Y-Z complies with the right-hand rule. X, Y and Z axes are fixed to the coil on which the coordinates are defined.

As illustrated in FIG. 2, a ring coil driven by AC Current I generates a certain magnetic field at a given point with distance r from the center of the transmitting coil. $\vec{r}$ is the vector from the center of the dipole antenna to the given point. If $r \ll \lambda$, $\lambda$ is the wave length of the RF signal, then the amplitude of the field strength at that point can be expressed as:

$$\vec{B} = \frac{u_0 m}{4\pi r^3}(2\cos\theta \cdot \vec{a}_r + \sin\theta \cdot \vec{a}_\theta) \quad (1)$$

$u_0$ is the permeability of the space between the transmitting and receiving coils. $m = I\pi a^2 \vec{a}_z$ is the magnetic moment of the loop antenna. a is the radius of the antenna loop. I is the current in the antenna. $\vec{a}_z$ is the axial unit vector in the direction of z axis of the reference coordinates. As shown in FIG. 2, θ is the angle between vector r and the z axis of the transmitting coil. $\vec{a}_r$ and $\vec{a}_\theta$ are unit vectors in the directions of the vector r and the unit vector orthogonal to vector r, respectively.

Having a sensing coil at this point, the induced voltage sensed by the receiving coil can be calculated based on equation (1):

$$V = k\frac{1}{r^5}\left[3z\left(\begin{bmatrix}x\\y\\z\end{bmatrix} \cdot \begin{bmatrix}n_x\\n_y\\n_z\end{bmatrix}\right) - n_z r^2\right] \quad (2)$$

$$\vec{r} = [x, y, z]', r = \sqrt{x^2 + y^2 + z^2}$$

in which k is a constant determined by the permeability of the space between transmitting and receiving coils, transmitting frequency and power, and coil structures. x, y, z are the coordinates of the BION coil relative to the reference frame attached with the transmitting coil. $[n_x, n_y, n_z]$ is the vector that describes the orientation of the sensor coil relative to the transmitting coil. $n_x$, $n_y$, and $n_z$ are projection of the unit vector in the direction of the sensing coil on the axes of the reference frame.

Transmitter and Sensor Configuration

An alternating magnetic field generated by one or more external transmitting coils induces voltage in the antenna of the BION implant, which is a function of relative orientation and position between the antenna coil and the field transmitters. Each BION receiver coil detects the derivative of this reference field projected to the coil axis. Thus each transmitting coil and receiving coil pair provides constraint on one degree of freedom (DOF). To constrain six DOFs on position and orientation, the sensing system needs at least six such transmitting and receiving pairs; for example, 2 sensing coils and 3 transmitting coils that can provide 6 independent combinations. Because induced voltage in a sensing coil is independent of its axial rotation, only 5 DOFs can be resolved when the sensing is based on one sensing coil. A 2-axis MEMS accelerometer in the same capsule can detect the 6th DOF from the static effects of gravity (as long as the long axis of the implant is not oriented exactly vertically) and also provides some redundancy for magnetic sensing.

The 3-D position and orientation of a rigid body altogether contain 6 independent variables if the position and orientation of the transmitting coils are known. There are 3 variables, x, y, and z, which are coordinates of the receiving coil in the reference frame 1 (x1-y1-z1) as shown in FIG. 1 or FIG. 4. Besides, the 3-D orientation of a rigid body can be decomposed into 3 Euler angles, $\alpha$, $\beta$, and $\gamma$, which are commonly known as roll, pitch, and yaw angles. Or the orientation can be described with quaternions to avoid singularities. As a 3-D rotation operator a quaternion also contains 3 independent variables. If we are only interested in the orientation of the receiving coil instead of the rigid body that the coil is attached to, we can just use two variables, 0 and 0, which are the receiving coil angles with respect to coordinate 1. The orientation transformation between the reference frame and the coordinate attached with the rigid body can be described with a rotation matrix or a quaternion.

So the position and orientation of a rigid body can be described with six independent variables, x, y, z, $\alpha$, $\beta$, and $\gamma$. To solve these six variables we need at least six equations. Equation (2) says that one transmitting coil and one receiving coil can make one non-linear equation. Therefore to calculate 6 variables we need the product of the number of the transmitter and the receiver to be 6. The least configuration can be 2 transmitters, 3 receiving coils, or
3 transmitters, 2 receiving coils, or
1 transmitters, 6 receiving coils, or
6 transmitters, 1 receiving coils In most FES application, multiple BIONs will be in each limb segment. If they are non-colinear magnetic sensing alone can detect all 6 DOFs. A successful FES system usually takes more than 2 sensor-stimulator implants to function because human limb joints are controlled by complimentary muscle groups. Because it is desirable to employ as few implants as possible, it is more desirable to add in more transmitters if there are no other constraints. In the following we make the assumption that there are 3 transmitters and 2 receiving coils. But the derived method can be easily extended to other different configurations. Increasing the number of transmitters or receiving coils can provide redundancy that can be used to minimize sensor noise with sensor fusion filters.

It may also be difficult to keep the relative orientation and position of the implants fixed. This is because of the implants being normally injected into different muscles that slide with respect to the skeleton and each other. Exemplary embodiments of the position and orientation detecting devices also provide a method to calibrate empirically and to correct mathematically for such posture-dependent motion of individual BION implants.

Sensing Position and Orientation with Distributed Receiving Coils and Lumped Transmitters The minimum setup for the sensing system should produce six equations to make the problem solvable. But the clinical scenario is different from patient to patient. Many possible configurations can be chosen to fit the clinical requirements.

The RF transmitters are outside of the human body, where we can have more space and more freedom in arranging the hardware. The first configuration of the sensing system is to have the transmitting antennas be lumped at the same location and they are arranged to be orthogonal in orientation as shown in FIG. 1. In FES applications these transmitting coils can be installed on the back of the wheelchair of the paralyzed patient. Another configuration is to have the transmitters located in different places. This configuration is most suitable for patient who needs many external RF coils for his/her muscle stimulator. The RF coils can be re-used as the magnetic field source for the sensor system. This situation gives a more complicated but solvable optimization problem.

The magnetic fields produced and detected in this sensing system were not significantly affected by nearby metal objects as long as they did not come between the reference field transmitters and implanted sensors. Distortion effects arise from the induction of eddy currents in the metal objects, which then generate their own magnetic fields, distorting the field to be sensed. The received signal declines rapidly with distance from the transmitting coils (generally with the distance cubed), so it is advantageous to position the transmitting coils so that they are generally close to but at varying distances from the various sensors implanted in the limb.

Many candidates for FES to reanimate the arm and hand are confined to wheelchairs, e.g. quadriplegia following spinal cord injury. The sensing scheme has a transmitting box that can be installed on the armrest of a wheelchair (FIG. 2). Multiple coils are installed on the box with different positions and orientations. For a single BION sensor, the number of transmitting coils should be higher than five. Increasing the number of transmitting coils adds redundancy and facilitates computation.

By locating the transmitting coils in the armrest, it is unlikely that large metal objects will come between transmitting and sensing coils. One exception, however, is the transmitting coil that powers the implant, which is designed to be worn on the arm itself. We have demonstrated that the electromagnetic effects of this coil are negligible if this coil is disconnected from its driver circuitry by an electronic switch for the brief intervals during which position measurements are made.

Configuration 1: Lumped Transmitters and Distributed Sensors

In this configuration, there are two possible outcomes depending on the clinical condition of a patient. The implanted BIONs could be in close proximity to each other or they could be far from each other.

In case the BIONs are in close proximity, if we turn on the orthogonal transmitting coils in sequence, we can measure six voltages from two BION sensing coils according to equation (2).

$$\begin{cases} V_{T1\_R1} = [(3x_1^2 - r_1^2) \cdot n_{x1} + 3x_1 \cdot y_1 \cdot n_{y1} + 3x_1 \cdot z_1 \cdot n_{z1}] \cdot k/r_1^5 \\ V_{T2\_R1} = [3x_1 \cdot y_1 \cdot n_{x1} + (3y_1^2 - r_1^2) \cdot n_{y1} + 3y_1 \cdot z_1 \cdot n_{z1}] \cdot k/r_1^5 \\ V_{T3\_R1} = [3x_1 \cdot z_1 \cdot n_{x1} + 3y_1 \cdot z_1 \cdot n_{y1} + (3z_1^2 - r_1^2) \cdot n_{z1}] \cdot k/r_1^5 \\ V_{T1\_R2} = [(3x_2^2 - r_2^2) \cdot n_{x2} + 3x_2 \cdot y_2 \cdot n_{y2} + 3x_2 \cdot z_2 \cdot n_{z2}] \cdot k/r_2^5 \\ V_{T2\_R2} = [3x_2 \cdot y_2 \cdot n_{x2} + (3y_2^2 - r_2^2) \cdot n_{y2} + 3y_2 \cdot z_2 \cdot n_{z2}] \cdot k/r_2^5 \\ V_{T3\_R2} = [3x_2 \cdot z_2 \cdot n_{x2} + 3y_2 \cdot z_2 \cdot n_{y2} + (3z_2^2 - r_2^2) \cdot n_{z2}] \cdot k/r_2^5 \end{cases} \quad (3)$$

$V_{Ti\_Rj}$ means the voltage sensed by receiving coil j when transmitting coil i is excited. If the two receiving coils are installed or implanted close enough compared with their distance from the transmitter, we can assume $$x_2 = x_1 = x;\ y_2 = y_1 = y;\ z_2 = z_1 = z;\ r_2 = r_1 = r \quad (4)$$

Then we have nine unknown variables:

$$x, y, z, n_{x1}, n_{y1}, n_{z1}, n_{x2}, n_{y2}, n_{z2}$$

The constraints are:

$$\begin{cases} n_{x1}^2 + n_{y1}^2 + n_{z1}^2 = 1 \\ n_{x2}^2 + n_{y2}^2 + n_{z2}^2 = 1 \\ \begin{bmatrix} n_{x2} \\ n_{y2} \\ n_{z2} \end{bmatrix} = R_1^2 \begin{bmatrix} n_{x1} \\ n_{y1} \\ n_{z1} \end{bmatrix} \\ -1 \le n_{x1}, n_{y1} \ldots n_{z2} \le 1; \end{cases} \quad (5)$$

If the actual measured voltages from the BION coils are $$VM_{T1\_S1-S2}, VM_{T2\_S1-S2}, VM_{T3\_S1-S2} \quad (6)$$

Then we can define an object function:

$$F = \sum_{j=1}^{3} \sum_{i=1}^{2} (VM_{Tj\_Si} - V_{Tj\_Si})^2 \quad (7)$$

The challenge then is to apply a nonlinear optimization process to minimize F, subject to the constraints in equation (5). The problem has local minimums, which require global optimization techniques.

In case that the two BIONs are injected and placed far from each other, the assumption of equation (4) would not hold. We then have to modify the constraints to include position information:

$$\begin{bmatrix} n_{x2} \\ n_{y2} \\ n_{z2} \\ 1 \end{bmatrix} = \begin{bmatrix} R_1^2 & P_1^2 \\ 0 & 1 \end{bmatrix} \begin{bmatrix} n_{x1} \\ n_{y1} \\ n_{z1} \\ 1 \end{bmatrix} \quad (8)$$

$$[x_2, y_2, z_2] = [x_1, y_1, z_1]' + P_1^2$$

$P_1^2$ is the vector between sensing coils. The optimization is the same after the above modification. The rotation matrix $R_1^2$ and the position vector $P_1^2$ can be determined by X-ray 2-D projection following BION injection. Both lumped and distributed RF magnetic sensors can be integrated with the Extended Kalman Filter to suppress noise.

The optimization and filtering process will generate the position [x, y, z]' and orientation $[n_x, n_y, n_z]'$, which can be converted into Euler angle or polar angles. This information can be further used to compute human limb postures.

Configuration 2: Distributed Transmitters and Sensors

In FES biomedical engineering applications, the BION implants work as muscle stimulators at the same time. In this case there is a RF transmitter for each group of these implants. It is therefore desirable to have these transmitters be re-used for RF magnetic sensors. This can be arranged at different place on a wheelchair according to medical requirements. This is the situation when both transmitters and receivers of the sensing system are distributed and non-orthogonal.

In the second configuration of the sensing system, the transmitting antennas are placed at different locations and in different orientation, if necessary.

Figure 3:
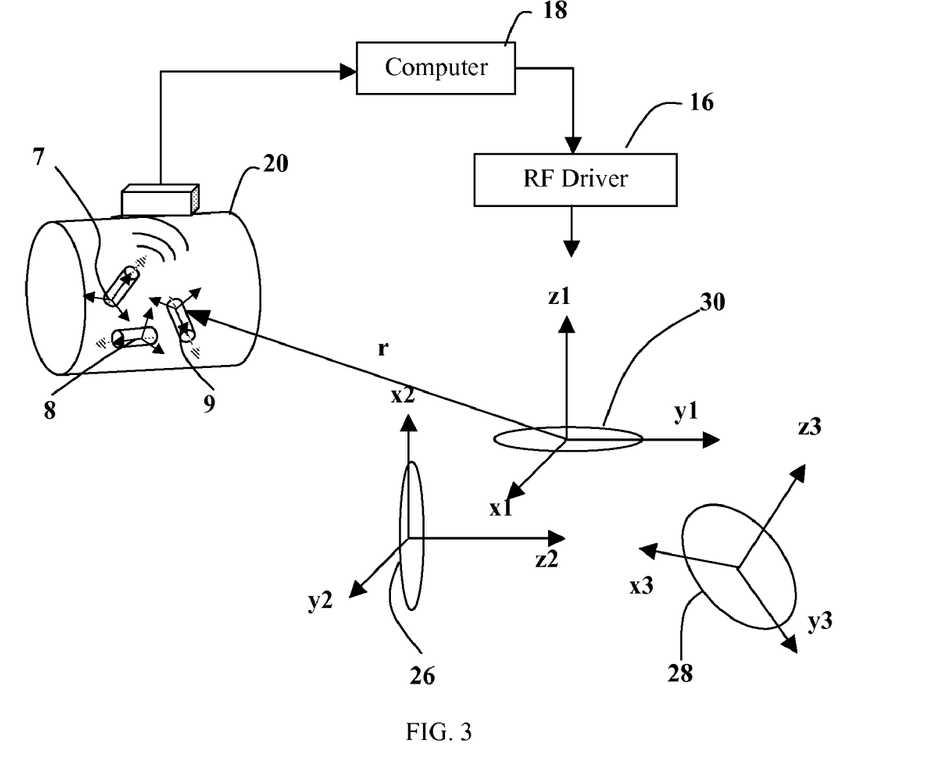
FIG. 3 is a diagram of the position and orientation sensing system with distributed RF magnetic sensors and transmitters.

As illustrated in FIG. 3, the sensed voltage of a sensing coil can be expressed as $$V_{Ti\_Rj} = k \frac{1}{r_{ji}^5} \left[ 3z_{ji} \left( \begin{bmatrix} x_{ji} \\ y_{ji} \\ z_{ji} \end{bmatrix} \cdot \begin{bmatrix} n_{xji} \\ n_{yji} \\ n_{zji} \end{bmatrix} \right) - n_{zji} r_{ji}^2 \right] \quad (9)$$

$$\vec{r}_{ji} = [x_{ji}, y_{ji}, z_{ji}]',\ r_{ji} = \sqrt{x_{ji}^2 + y_{ji}^2 + z_{ji}^2}$$

The subscript of ji means the jth sensing coil with respect to the ith reference frame. Equation (9) can be constructed for each transmitter-receiver pair to make a 6-equation group.

The relationship of the distributed transmitting coil positions can be expressed as 4-dimension rotation matrices. For example:

$$\vec{p}_{11} = \begin{bmatrix} R_2^1 & P_2^1 \\ 0 & 1 \end{bmatrix} \vec{p}_{12}$$

in which $\vec{p}_{11} = [x_{11}, y_{11}, z_{11}, 1]'$; $\vec{p}_{12} = [x_{12}, y_{12}, z_{12}, 1]'$ are the extended coordinates of the origin of the sensor frame 1 (26) (attached to sensor 1) described in reference frame 1 (26) and 2 (28) respectively. $R_2^1$ is the rotation transform matrix from reference frame 1 (26) to frame 2 (28). $P_2^1$ is the vector from the origin of reference frame 1 (26) to the origin of reference frame 2 (28). The same notation method can be applied to frame 3 (30).

Similarly the rotation relationship between different reference frames can also be expressed with 3-dimension rotation matrices. For example:

$$\vec{n}_{11} = R_2^1 \vec{n}_{12}$$

in which $\vec{n}_{11} = [n_{x11}, n_{y11}, n_{z11}]'$, $\vec{n}_{12} = [n_{x12}, n_{y12}, n_{z12}]$.

With these transformations the problem can be described as a similar optimization problem with the last configuration. Even though the second configuration means more variables and constraints, basically it is still the same optimization problem with the configuration one. Similarly the global optimization technique can be used to compute the posture at a single time interval. Then the Extended Kalman Filter can be used to reduce noise.

Signal Processing Techniques

U.S. Pat. No. 6,690,963 described the signal processing problem for multi-transmitter and sensor as solving a non-linear equation group with numerical methods such as Newton-Raphson method and Broyden's method. These traditional gradient based methods work only when the transmitters and receivers are properly located and orientated. Basically the nonlinear optimization problem presents local minimum areas. To find the solution for a wider range of system configurations, we have to look into global optimization techniques.

The problem of extracting position and orientation information from the sensors is a global non-linear optimization problem. The object function in equation (7) has many local minimums. Global optimization techniques such as genetic algorithm and simulated annealing can avoid local minimum points and get the solution equal or close to the true solution. Genetic algorithm (U.S. Pat. No. 5,255,345) and simulated annealing are typical global optimization methods that can be employed as a part of the signal processing stage. For the specific problem we are working on, genetic algorithm presents pretty good performance in bringing the solutions close to the true minimum point. To deal with the inequality and equality constraints as shown in equation (5), we can either use a constrained genetic algorithm or we can convert the problem into a non-constrained problem by combining the constraints with the objective function. The implementation of a genetic algorithm should be familiar to people with expertise in related area.

However, genetic algorithm does not work well in asymptotic convergence, while traditional gradient-based optimization techniques are good at this job. To take advantage of both of these techniques, we can combine these into two steps. In the first step we use genetic algorithm to avoid local minimums and get close to the true minimum point. In the second step we can use traditional optimization techniques known as prior art to achieve asymptotic convergence. Similar with the genetic algorithm, both constrained and non-constrained optimization techniques can be employed to solve the problem. In our simulation, it takes less than 80 generations of genetic algorithm and 100 iterations of the traditional optimization to achieve error level better than 1%.

Figure 7:
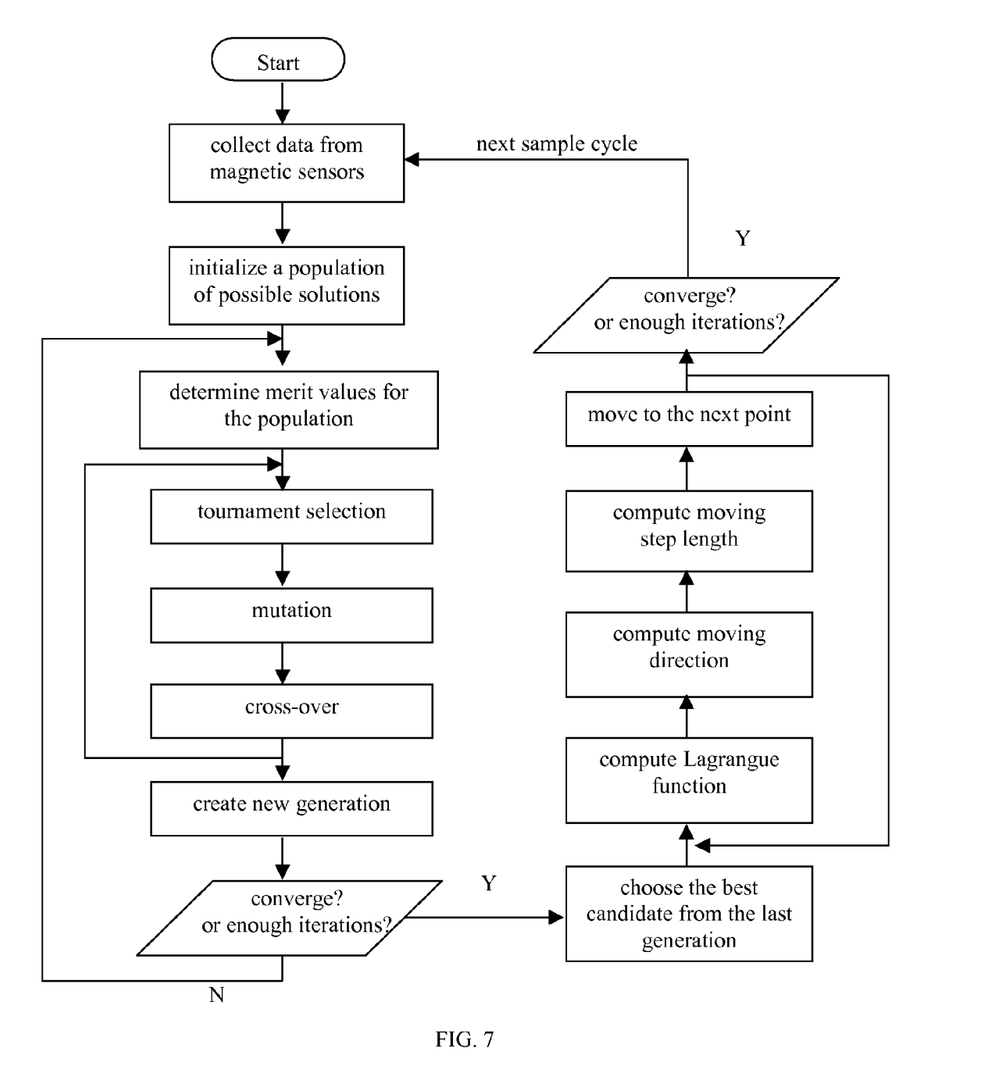
FIG. 7 is the flowchart of global optimization algorithm.

FIG. 7 illustrates the above global optimization technique. Typical genetic operations of population selection, mutation, and cross-over algorithms are explained in many papers and books.

Figure 6:
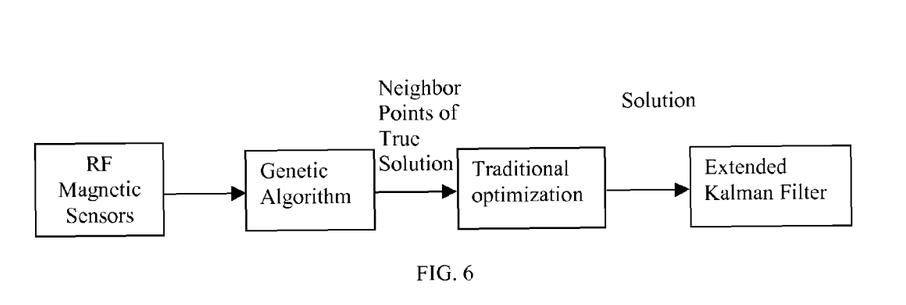
FIG. 6 is a diagram of the cascaded signal processing steps.

The sensor signal can never be noise free since environmental electromagnetic interference and non-ideal transmitter and receiver shapes. Extended Kalman filter can be employed to this nonlinear system to suppress noise. Kalman filter can also make use of the movement history information and help to avoid the algorithm being trapped in singularities. The overall signal processing diagram is shown in FIG. 6. According to our experience, a microcomputer whose processing capability is on the level of a Pentium III should be able to easily implement the algorithm in real time with a sample rate of over 500 sample points per second.

Judge Signal Phase with Synchronized Transmitters

The orientations of the receiving coils with respect to the transmitting coils are not only reflected by the amplitude of the sensed signal, but also described by the phase of the sensed signal. Specifically, if the sensed signal is in the same phase with the transmitted signal, then the sensing coil should orientate within +/−90 degree of the transmitting coil flux tangent. Otherwise the sensing coil should orientate in the other direction, i.e. 90-270 degrees with respect to the transmitting coil flux tangent. The conclusion in the last paragraph is based on the assumption that the sign of the voltage V in equation (2) can be detected. Therefore the phase of the sensed signal contains important information about the coil orientation. To judge the coil, we propose the synchronizing method as shown in FIG. 8.

For a typical wireless FES treatment, the patient needs an external transmitting coil to provide power and command signal wirelessly to the implanted muscle stimulator. If we synchronize the signal from this coil and the transmitting antenna for the RF magnetic sensor, we will be able to tell the phase of the sensed signal.

Figure 8:
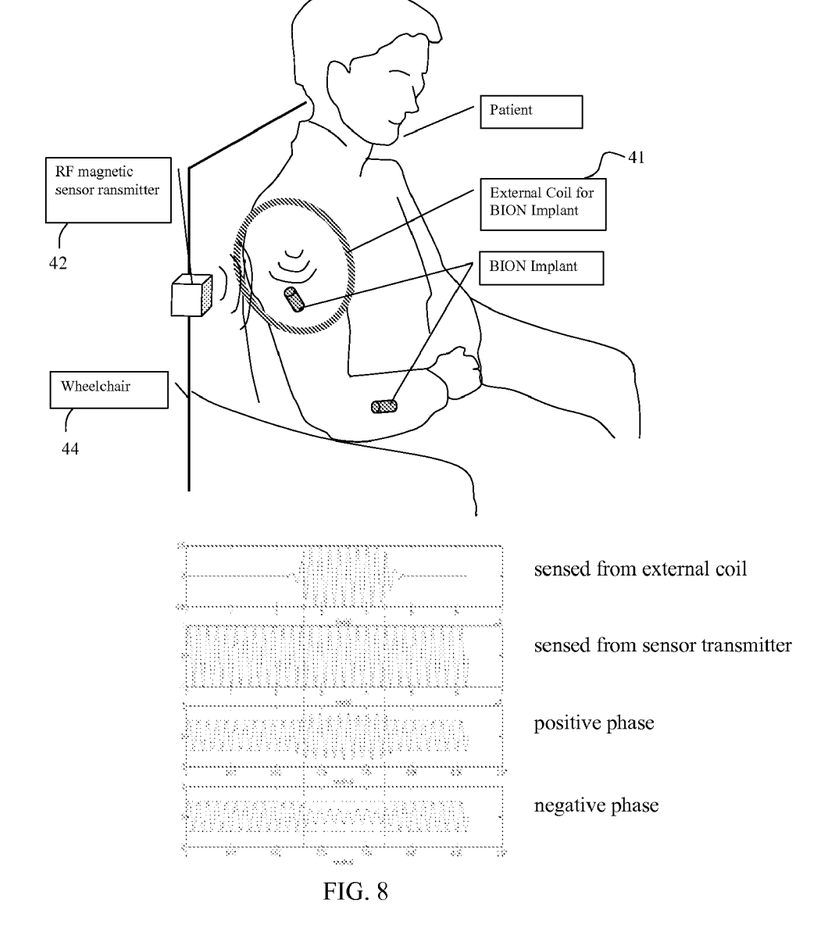
FIG. 8 is the scheme for the sensor to judge the phase of the RF magnetic signal.
Figure 12:
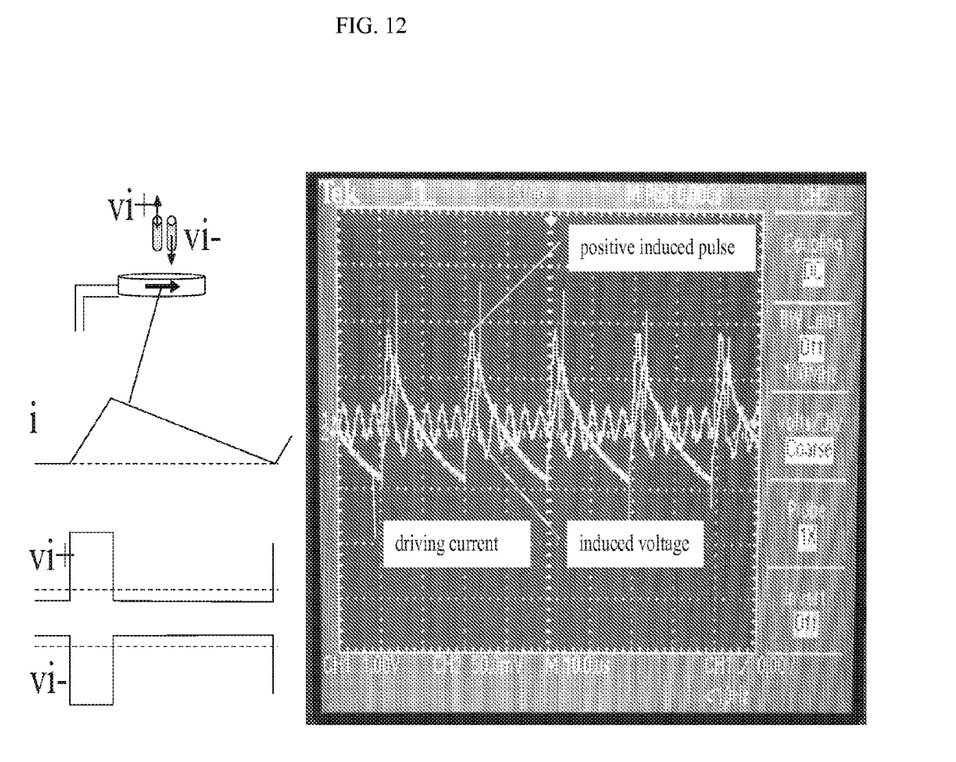
FIG. 12 illustrates an alternative scheme to determine the phase of a magnetic signal.

As illustrated in FIG. 8, an external coil 41 and a transmitting antenna 42 can be designed to be excited in different but synchronized time intervals. When the magnetic field transmitting antenna 42 is on and the signal sensed by the sensing coil reaches steady state, the external FES coil is excited for a short time interval. During this interval, if the external coil weakens the sensed signal, then the sensing coil is a different phase with the magnetic field transmitting coil; otherwise the sensing coil is in the same direction with the magnetic field transmitting coil. The phase information actually tells the sign of the sensed magnetic field. With the phase the voltage V sensed in equation (2) can be positive or negative according to the relative position and orientation of the transmitting coil and the sensing coil. An alternative method to determine the phase of the magnetic signal (and hence the absolute orientation of the sensor) is illustrated in FIG. 12.

This problem can be solved with a pulsed current generator such as can be produced by rapidly discharging a capacitor in a relaxation oscillator. The induced voltage on the BION sensing coil is negatively proportional to the time derivative of the flux and therefore the derivative of the current driving the external coil. If the driving current is an asymmetrical "sawtooth", then the faster first (positive) phase will generate a larger magnitude voltage in the sensing coil than the slower second (negative). The sign of the larger peak tells which direction the sensing coil is oriented with respect to the transmitting coil (see +/−voltage peaks in FIG. 12). In reality because the BION sensing coil is tuned to resonate at 480 kHz, the step voltage actually will be a smooth pulse with harmonic ripples, as measured experimentally (the right side of FIG. 12). Nevertheless, the peak of the pulse will indicate both the sign and amplitude of the induced voltage.

Wireless Design

Figure 9:
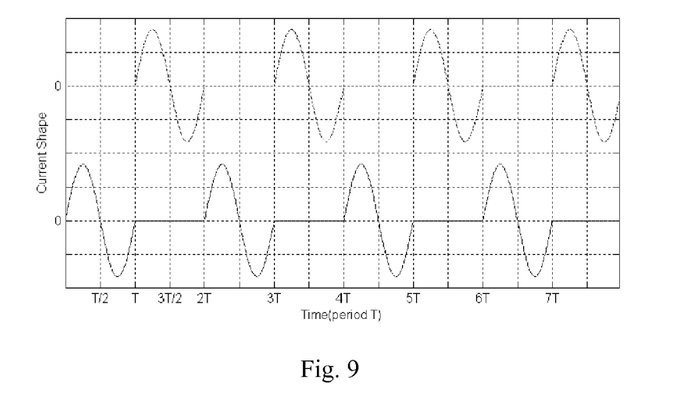
FIG. 9 is the current shape for the implant to generate f/2 back-telemetry signal.

The BION implants are wireless capsules. The power and control signal are delivered wirelessly from an external coil. The detailed technique has been shown in U.S. Pat. Nos. 5,193,540; 5,324,316; 5,312,439 and 6,175,764. To send the signal out without significant power consumption, passive back-telemetry technique can be used. The implementation details are familiar to people who are experts in this area. A preferable implementation for the implant is to switch the received current into wave sequences as shown in FIG. 9. The two waveforms in FIG. 9 contain half-frequency harmonics, which will induce half-frequency voltage on the external coil. By applying strong filters on the external coil side, signal modulated with the half-frequency harmonic can be detected.

Cancel Muscle Deformation

The BION implants are designed to be injected into human muscles. The musculoskeletal system of the arm is actually not a rigid body, as assumed by the above algorithm. BIONs implanted in the muscles will move with respect to each other as the arm rotates.

If we install the BIONs properly into a pair of complementary muscles, we can keep their relative rotation and movement as small as possible. However the magnetic sensor is very sensitive to orientation change for certain angle range. A slight relative rotation might cause big error in measurement. If we can address the muscle deformation in our algorithm, we should be able to limit this error.

Figure 10:
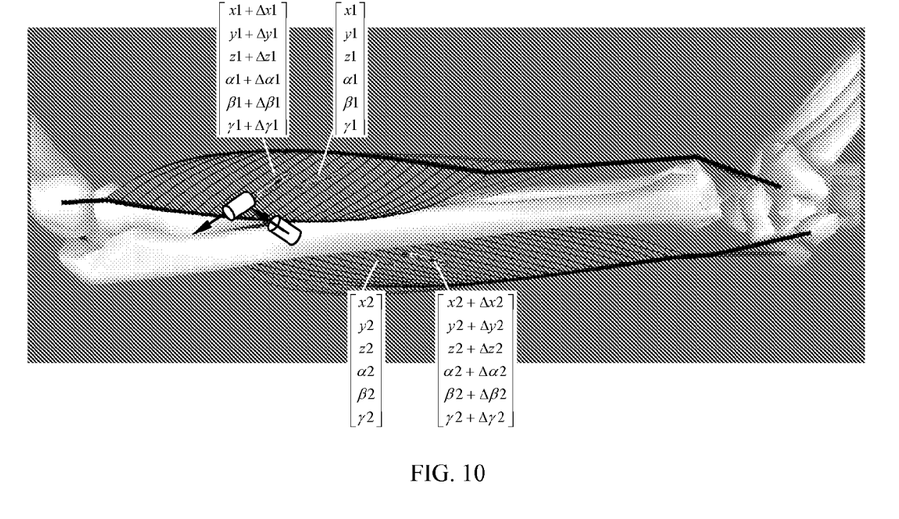
FIG. 10 shows a musculoskeletal model of the human arm and two implanted BIONs.

The musculoskeletal model of the human arm and two implanted BIONs are shown in FIG. 10. We define the initial position of the arm as vertically straight. BION1 has the initial position and orientation of [x1, y1, z1, α1, β1, γ1], and BION2 is [x2, y2, z2, α2, β2, γ2]. As the arm rotates, the BIONs will move with the muscles and they will also move in the muscles as the muscles deform. Considering the deviation from their initial positions and orientations, the resulted position and orientation after the rotation can be written as [x1+Δx1, y1+Δy1, z1+Δz1, α1+Δα1, β1+Δβ1, γ1+Δγ1] and [x2+Δx2, y2+Δy2, z2+Δz2, α2+Δα2, β2+Δβ2, γ2+Δγ2], as shown in FIG. 10. The delta values are nonlinear functions of the rotation angles of the arm. Using Euler angles, these values can be expressed as:

$$\begin{bmatrix} \Delta x1 \\ \Delta y1 \\ \vdots \\ \Delta \beta 2 \\ \Delta \gamma 2 \end{bmatrix}_{12\times 1} = \begin{bmatrix} f_{x1}(\alpha, \beta, \gamma) \\ f_{y1}(\alpha, \beta, \gamma) \\ \vdots \\ f_{\beta 2}(\alpha, \beta, \gamma) \\ f_{\gamma 2}(\alpha, \beta, \gamma) \end{bmatrix}_{12\times 1} \quad (10)$$

$$\approx \begin{bmatrix} \frac{\partial f_{x1}}{\partial \alpha} & \frac{\partial f_{x1}}{\partial \beta} & \frac{\partial f_{x1}}{\partial \gamma} \\ \frac{\partial f_{y1}}{\partial \alpha} & \frac{\partial f_{y1}}{\partial \beta} & \frac{\partial f_{z1}}{\partial \gamma} \\ \cdots & \cdots & \cdots \\ \frac{\partial f_{\beta 2}}{\partial \alpha} & \frac{\partial f_{\beta 2}}{\partial \beta} & \frac{\partial f_{\beta 2}}{\partial \gamma} \\ \frac{\partial f_{\gamma 2}}{\partial \alpha} & \frac{\partial f_{\gamma 2}}{\partial \beta} & \frac{\partial f_{\gamma 2}}{\partial \gamma} \end{bmatrix}_{12\times 3} \begin{bmatrix} \alpha \\ \beta \\ \gamma \end{bmatrix}$$

$$= F \begin{bmatrix} \alpha \\ \beta \\ \gamma \end{bmatrix}$$

We used linear approximation to write the nonlinear functions into the product of a constant matrix F, which is Jacobian matrix of the nonlinear functions, and a vector which describes the rotation of the bone. If we know the constant matrix F, we will be able to tell how much the BIONs deviate from their initial positions and orientations.

The matrix F can be measured experimentally from a large group of redundant data. Assuming we sampled n points from different postures, from equation (10) we can write the following equation:

$$F = \qquad (11)$$

$$\begin{bmatrix} \Delta x1(1) & \Delta x1(2) & \cdots & \Delta x1(n) \\ \Delta y1(1) & \Delta y1(2) & \cdots & \Delta y1(n) \\ & \vdots & & \\ \Delta \beta 2(1) & \Delta \beta 2(2) & \cdots & \Delta \beta 2(n) \\ \Delta \gamma 2(1) & \Delta \gamma 2(2) & \cdots & \Delta \gamma 2(n) \end{bmatrix}_{12\times n} \left( \begin{bmatrix} \alpha(1) & \alpha(2) & \cdots & \alpha(n) \\ \beta(1) & \beta(2) & \cdots & \beta(n) \\ \gamma(1) & \gamma(2) & \cdots & \gamma(n) \end{bmatrix}^{+} \right)_{n\times 3}$$

The + operator is the pseudo-inverse of a matrix, which provides a linear approximation of the matrix F.

With the linear approximation, we can re-write the optimization problem as:
Find x1, y1, z1, x2, y2, z2, α, β, γ (or q0~q4 with quoternions) to minimize $$FA = \sum_{j=1}^{3} \sum_{i=1}^{2} (VM_{Tj\_Si} - V_{Tj\_Si})^2 \qquad (12)$$

$$s.t. \quad R_{1\ new}^{ref} = R_{2\ new}^{ref} R_{1\ new}^{2} = R_{2\ new}^{ref} R_{\Delta 1} R_{1\ old}^{2} R_{\Delta 2}'$$

$R_{1\ new}^{ref}$ is the rotation matrix of sensing coil 1 w.r.t. the reference frame after the Δα1-Δβ1-Δγ1 rotation. $R_{\Delta 1}$ is the rotation matrix of sensing coil 1 w.r.t. the coil frame before Δα1-Δβ1-Δγ1 rotation. Other annotations have similar meanings.

With equation (12) the orientation of coil1 after muscle deformation can be written as:

$$\begin{bmatrix} n_{x1} \\ n_{y1} \\ n_{z1} \end{bmatrix}_{new} = R_{1\ new}^{ref} \begin{bmatrix} 0 \\ 0 \\ 1 \end{bmatrix} = R_{2\ new}^{ref} R_{\Delta 1} R_{1\ old}^{2} R_{\Delta 2}' \begin{bmatrix} 0 \\ 0 \\ 1 \end{bmatrix} \qquad (13)$$

and $$\begin{bmatrix} x_1 \\ y_1 \\ z_1 \end{bmatrix}_{new} = \begin{bmatrix} x_2 \\ y_2 \\ z_2 \end{bmatrix}_{new} + R_{1\ new}^{ref} \begin{bmatrix} \Delta x_2 - \Delta x_1 \\ \Delta y_2 - \Delta y_1 \\ \Delta z_2 - \Delta z_1 \end{bmatrix}_1 \qquad (14)$$

Plug (13) and (14) into equation (12) we can go through the same optimization process described above and solve the position and orientation of the bone with muscle deformation linearly cancelled.

Figure 11:
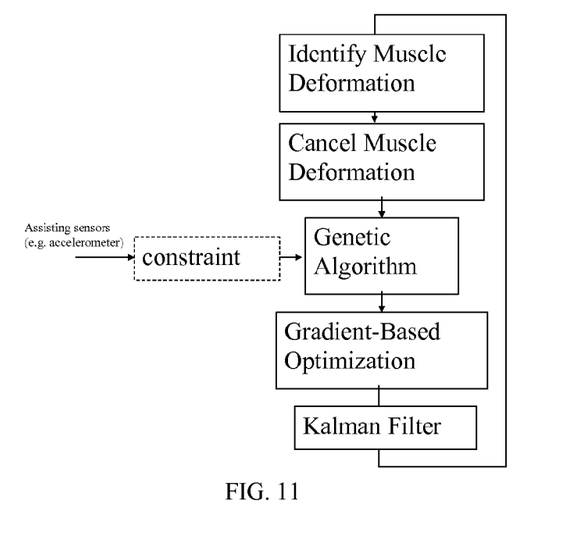
FIG. 11 illustrates an algorithm chart for composite optimization algorithm.

FIG. 11 illustrates an algorithm chart for composite optimization algorithm. Other assisting sensors integrated in BION assembly, such as MEMS accelerometers and EMG sensors, can provide helpful information. But because the information is usually noisy and incomplete, it can be used as constraints on certain variables based on their properties of random distribution. The constraints will be integrated in the 2-step optimization process to find the solution.

Appendices I and II hereto set forth further information about magnetic field generation and measurement and calibration and integration; the contents of these appendices are incorporated herein by reference.

The previous description of the disclosed embodiments is provided to enable any person skilled in the art to make or use the position and orientation detection devices. Various modifications to these embodiments will be readily apparent to those skilled in the art, and the generic principles defined herein may be applied to other embodiments without departing from the spirit or scope of the position and orientation detection devices, methods and systems. Thus, the position and orientation detection devices, methods and systems are not intended to be limited to the embodiments shown herein but are to be accorded the widest scope consistent with the principles and novel features disclosed herein.

The invention claimed is:

1. A position and orientation detecting system to measure movement of a limb described with six independent position and orientation variables, comprising:
 a) one magnetic field source, comprising an AC source and a transmitter coil energized by an asymmetrical current waveform, configured to be located external to the limb and to generate at least one magnetic field;
 b) six physically separated, non-orthogonally oriented capsules configured to be implanted within the limb, each capsule having a sensor configured to sense the magnetic field and to telemetrically transmit at least one signal corresponding to the sensed magnetic field, wherein the transmitted signal comprises phase data; and c) a controller configured to receive the transmitted signals, to compute the position and orientation of the limb based on the transmitted signals, and to generate information useful in controlling movement of the limb based on the transmitted signals;

wherein the product of the number of the magnetic field source and the capsule is six.

2. The system of claim 1, wherein the phase data is determined from the sign of the largest signal sensed by the sensor that transmitted the phase data.

3. The system of claim 1, wherein each sensor includes a sensor coil to sense the magnetic field.

4. The system of claim 3, wherein each sensor coil is configured to also function as an antenna for a limb stimulator.

5. The system of claim 4, wherein the transmitter coil is configured to also function as an antenna to transmit data to a limb stimulator.

6. The system of claim 5, wherein each sensor coil is implanted within the limb at a location that is based on a clinical application.

7. The system of claim 3, wherein each sensor coil is orientated non-orthogonally relative to the other sensor coils and/or the transmitter coil.

8. The system of claim 7, wherein the controller comprises a composite optimization algorithm and is configured to solve for a constraint involved in configuring the coils.

9. The system of claim 3, wherein the controller is configured to apply a global optimization algorithm to minimize local minimum points.

10. The system of claim 9, wherein the global optimization technique comprises a genetic algorithm.

11. The system of claim 10, wherein the global optimization technique further comprises a gradient-based optimization technique.

12. The system of claim 3, wherein the controller comprises a linear approximation technique to cancel muscle deformation.

13. The system of claim 3, wherein the transmitter coil is positioned at a location that is based on a clinical application.

14. The system of claim 13, wherein the transmitter coil is placed at a different location.

15. The system of claim 1, wherein each sensor comprises a single coil wrapped around two ferrite rods, an integrated circuit chip and a micro-PCB board.

16. The system of claim 15, wherein each capsule includes a stimulator assembly configured to provide stimulation of limb muscle.

17. The system of claim 1, wherein one of the capsules has a 2-axis MEMS accelerometer to detect the static effects of gravity.

18. The system of claim 1, wherein the controller is further configured to reduce noise by using an Extended Kalman Filter.

* * * * *